US00PP14932P2

(12) United States Plant Patent
Wain

(10) Patent No.: US PP14,932 P2
(45) Date of Patent: Jun. 22, 2004

(54) CHRYSANTHEMUM PLANT NAMED 'MATISSE'

(50) Latin Name: *Chrysanthemum×morifolium*
Varietal Denomination: Matisse

(75) Inventor: Peter Wain, Locksheath (GB)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/396,547

(22) Filed: Mar. 25, 2003

(51) Int. Cl.[7] ..... A01H 5/00
(52) U.S. Cl. ..... Plt./297
(58) Field of Search ..... Plt./297

*Primary Examiner*—Anne Marie Grunberg
(74) *Attorney, Agent, or Firm*—C. A. Whealy

(57) ABSTRACT

A distinct cultivar of Chrysanthemum plant named 'Matisse', characterized by its upright, outwardly spreading and mounded plant habit; freely branching habit; uniform and freely flowering habit; anemone-type inflorescences with quill-shaped ray florets; light purple-colored ray and disc florets; and natural season flowering in mid-October in the Northern Hemisphere.

1 Drawing Sheet

Botanical classification/cultivar designation: *Chrysanthemum×morifolium* cultivar Matisse.

BACKGROUND OF THE INVENTION

The present invention relates to a new and distinct cultivar of Chrysanthemum plant, botanically known as *Chrysanthemum×morifolium,* commercially known as a garden-type Chrysanthemum and hereinafter referred to by the name 'Matisse'.

The new cultivar is a product of a planned breeding program conducted by the Inventor in Fareham, United Kingdom. The objective of the breeding program is to create new garden-type Chrysanthemum cultivars having inflorescences with desirable inflorescence forms, attractive floret colors and good garden performance.

The new Chrysanthemum originated from a cross made in March, 1997, in Fareham, United Kingdom, of a proprietary seedling selection of *Chrysanthemum×morifolium* identified as code number 03W 4, not patented, as the female, or seed, parent with the *Chrysanthemum×morifolium* cultivar Empire Citrine, disclosed in U.S. Plant Pat. No. 9,094, as the male, or pollen, parent. The new Chrysanthemum was discovered and selected by the Inventor as a single flowering plant within the progeny of the stated cross grown in a controlled environment in Fareham, United Kingdom in September, 1997. The selection of this plant was based on its desirable inflorescence form, attractive ray floret color and good garden performance.

Asexual reproduction of the new cultivar by terminal cuttings taken in a controlled environment in Fareham, United Kingdom since December, 1997, has shown that the unique features of this new Chrysanthemum are stable and reproduced true to type in successive generations.

SUMMARY OF THE INVENTION

The cultivar Matisse has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Matisse'. These characteristics in combination distinguish 'Matisse' as a new and distinct cultivar:

1. Upright, outwardly spreading and mounded plant habit.
2. Freely branching habit; dense and full plants.
3. Uniform and freely flowering habit.
4. Anemone-type inflorescences with quilled ray florets.
5. Light purple-colored ray and disc florets.
6. Natural season flowering in mid-October in the Northern Hemisphere.

In side-by-side comparisons conducted in Fareham, United Kingdom, plants of the new Chrysanthemum differed from plants of the female parent seedling selection, in the following characteristics:

1. Plants of the new Chrysanthemum had a more uniform plant growth habit than plants of the female parent seedling selection.
2. Plants of the new Chrysanthemum flowered more slowly than plants of the female parent seedling selection.
3. Ray florets of inflorescences of plants of the new Chrysanthemum were lighter purple in color than ray florets of inflorescences of plants of the female parent seedling selection.

In side-by-side comparisons conducted in Fareham, United Kingdom, plants of the new Chrysanthemum differed from plants of the male parent, the cultivar Empire Citrine, in the following characteristics:

1. Plants of the new Chrysanthemum were more compact than plants of the cultivar Empire Citrine.
2. Plants of the new Chrysanthemum flowered more slowly than plants of the cultivar Empire Citrine.
3. Plants of the new Chrysanthemum had anemone-type inflorescences whereas plants of the cultivar Empire Citrine had daisy-type inflorescences.
4. Plants of the new Chrysanthemum and the cultivar Empire Citrine differed in ray floret coloration as plants of the cultivar Empire Citrine had yellow-colored ray florets.

Plants of the new Chrysanthemum can also be compared to plants of the Chrysanthemum cultivar Yomary-Jayne, disclosed in U.S. Plant patent application Ser. No. 10/094,267. In side-by-side comparisons conducted in Alva, Fla., plants of the new Chrysanthemum differed from plants of the cultivar Yomary-Jayne in the following characteristics:

1. Plants of the new Chrysanthemum were larger and more rounded than plants of the cultivar Yomary-Jayne.
2. Plants of the new Chrysanthemum flowered about two weeks later than plants of the cultivar Yomary-Jayne.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Matisse'.

The photograph at the bottom of the sheet comprises a close-up view of typical inflorescences of the cultivar 'Matisse'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Salinas, Calif., under natural season conditions and practices which approximate those generally used in commercial garden-type Chrysanthemum production. One cutting was planted in a 15.25-cm container in late May, 2002. Plants were not pinched, that is, the terminal apex was not removed to enhance branching. During the production of the plants, day temperatures averaged 20° C. and night averaged 13° C. Measurements and numerical values represent averages for typical flowering plants.

Botanical classification: *Chrysanthemum×morifolium* cultivar Matisse.

Commercial classification: Anemone-type garden Chrysanthemum.

Parentage:

*Female, or seed, parent.*—Proprietary seedling selection of *Chrysanthemum×morifolium* identified as code number 03W 4, not patented.

*Male, or pollen, parent.*—*Chrysanthemum×morifolium* cultivar Empire Citrine, disclosed in U.S. Plant Pat. No. 9,094.

Propagation:

*Type.*—Terminal tip cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Appearance.*—Perennial herbaceous anemone-type garden Chrysanthemum. Inverted triangle with rounded crown. Stems initially upright, then somewhat outwardly spreading giving a uniformly mounded appearance to the plant. Freely branching with lateral branches forming at every node.

*Plant height.*—About 23 cm.

*Plant diameter.*—About 31 cm.

*Lateral branches.*—Length: About 19 cm. Diameter: About 5 mm. Internode length: About 1.25 cm. Aspect: Upright and outwardly spreading. Texture: Pubescent. Color: 146A overlain with 187A.

*Foliage description.*—Leaf arrangement: Alternate. Length: About 6.2 cm. Width: About 4.75 cm. Apex: Cuspidate to mucronate. Base: Truncate. Margin: Palmately lobed, sinuses parallel to convergent. Texture, upper surface: Slightly pubescent. Texture, lower surface: Pubescent; veins prominent. Color: Developing and fully expanded foliage, upper surface: 147A. Developing and fully expanded foliage, lower surface: Slightly darker than 147B. Venation, upper surface: 147A to 147B. Venation, lower surface: 147B. Petiole length: About 1.8 cm. Petiole diameter: About 2.5 mm. Petiole color, upper surface: Close to 147B to 147C. Petiole color, lower surface: Close to 147B.

Inflorescence description:

*Appearance.*—Anemone-type inflorescence form with quilled-shaped ray florets. Inflorescences borne on terminals above foliage, arising from leaf axils. Disk and ray florets developing acropetally on a capitulum. About eight inflorescences per lateral.

*Flowering response.*—Under natural season conditions, plants flower in mid-October in the Northern Hemisphere.

*Inflorescence bud (before showing color).*—Height: About 5 mm. Diameter: About 8 mm. Shape: Oblate. Color (lower surface of phyllaries): Close to 147A.

*Inflorescence size.*—Diameter: About 5.5 cm. Depth (height): About 1.5 cm. Disc diameter: About 2.7 cm. Receptacle diameter: About 5 mm.

*Ray florets.*—Shape: Quilled. Length: About 2.75 cm. Corolla tube length: About 2.75 cm. Width: About 2.5 mm. Apex: Rounded or emarginate. Margin: Fused. Texture: Smooth, glabrous; satiny. Surface: Flat. Orientation: Initially upright, then about 80° from vertical. Number of ray florets per inflorescence: About 52 in one or two whorls. Color: When opening and fully opened, upper surface: Close to 155D overlain with 77A. When opening and fully opened, lower surface: Close to 155D underlain with 77A.

*Disc florets.*—Shape: Tubular; enlarged; apex dentate, five-pointed. Length: About 1.25 cm. Width, apex: About 3 mm. Width, base: About 1 mm. Number of disc florets per inflorescence: About 101. Color: Immature: Close to 154A. Mature: Apex: At apex, 154A to 5A; towards apex, close to 79A. Midsection: Close to 155D overlain with 77A. Base: Close to 150C. Throat: Close to 155D faintly overlain with 77A.

*Peduncle.*—Strength: Strong. Aspect: About 40° from vertical. Length: First peduncle: About 5.2 cm. Fourth peduncle: About 8.9 cm. Seventh peduncle: About 13 cm. Diameter: About 2 mm. Texture: Pubescent. Color: 146A overlain with 187A.

*Phyllaries.*—Quantity per inflorescence: About 24. Length: About 7 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 147A.

*Reproductive organs.*—Androecium: Present on disc florets only. Anther color: 9A. Pollen: None observed. Gynoecium: Present on both ray and disc florets.

*Seed/fruit.*—Seed and fruit production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 37° C.

It is claimed:

1. A new and distinct cultivar of Chrysanthemum plant named 'Matisse', as illustrated and described.

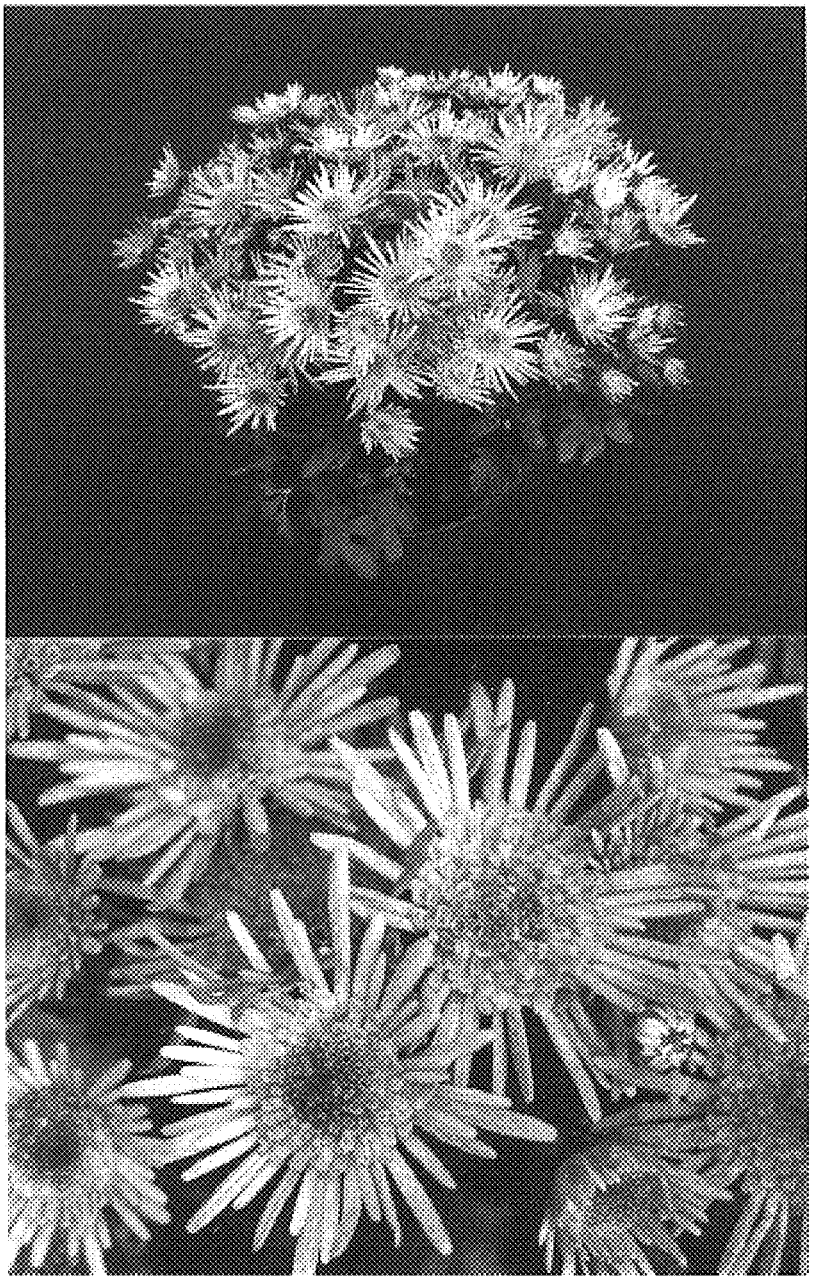

* * * * *